United States Patent [19]

Makari

[11] Patent Number: 4,752,471

[45] Date of Patent: Jun. 21, 1988

[54] CANCER DETECTION PREPARATIONS AND METHOD

[76] Inventor: Jack G. Makari, 88 Everett Road, Demarest, N.J. 07627

[21] Appl. No.: 370,517

[22] Filed: Apr. 21, 1982

Related U.S. Application Data

[63] Continuation-in-part of Ser. No. 925,469, Jul. 17, 1978, abandoned, which is a continuation-in-part of Ser. No. 812,069, Jul. 1, 1977, abandoned, which is a continuation of Ser. No. 31,855, May 1, 1970, abandoned, which is a continuation of Ser. No. 530,774, Mar. 1, 1966, abandoned, which is a continuation-in-part of Ser. No. 421,683, Dec. 28, 1964, abandoned, which is a continuation-in-part of Ser. No. 127,849, Jul. 31, 1961, abandoned, which is a continuation-in-part of Ser. No. 75,454, Aug. 26, 1959, abandoned.

[51] Int. Cl.$^4$ .............................................. A61K 49/00
[52] U.S. Cl. ......................................................... 424/9
[58] Field of Search ............................................. 424/9

[56] References Cited

PUBLICATIONS

British Medical Journal, Aug. 9, 1958, pp. 355–361.

Primary Examiner—Frederick E. Waddell
Attorney, Agent, or Firm—Darby & Darby

[57] ABSTRACT

A method for detecting cancer comprises intradermally injecting into a patient a test preparation comprising a glycoprotein-polysaccharide-like antigenic substance admixed with the patient's blood serum. The patient's serum is also injected intradermally as a control and the physical dimensions of the erythemas of the injections measured and compared as an indication of the presence of cancer.

An initial antigenic substance is derived from cancerous tissues by disintegrating the tissue to enable the separation of the nuclei and cell membranes from the mitochondrial fraction of the cell. After lipids are removed from the mitochondrial fraction, it is hydrolyzed in hot alkali, dialyzed and then deproteinated. The cancer specificity of the antigenic substance is enhanced by gel filtration.

Prior to admixture with the antigenic substance, the blood serum is subjected to an adsorptive procedure to remove non-cancerous antibodies which might otherwise be reactive with the antigenic substance. A proteolytic enzyme (e.g. trypsin) is added to a portion of the blood serum to provide, in the preferred embodiment, additional cancer detection preparations.

19 Claims, No Drawings

CANCER DETECTION PREPARATIONS AND METHOD

CROSS REFERENCE TO RELATED APPLICATIONS

This application is a continuation-in-part of copending application Ser. No. 925,469, filed July 17, 1978 (now abandoned), which is a continuation-in-part of the then copending (now abandoned) application Ser. No. 812,069 filed July 1, 1977, which is a continuation of the then copending (now abandoned) application Ser. No. 31,855 filed May 1, 1970, which in turn is a continuation of the then copending (now abandoned) application Ser. No. 530,774 filed Mar. 1, 1966, which is a continuation-in-part of the then copending (now abandoned) application Ser. No. 421,683, filed Dec. 28, 1964, which is a continuation-in-part of the then copending (now abandoned) application Ser. No. 127,849 filed on July 31, 1961, and which in turn is a continuation-in-part of the then copending (now abandoned) application Ser. No. 75,454, filed on Aug. 26, 1959. Each of the aforementioned applications is hereby incorporated by reference into this application.

FIELD OF THE INVENTION

The present invention relates to cancer detection preparations, their administration and their methods of manufacture.

Effective tests capable of detecting malignant cancer in its early stages remain a fundamental need and goal of medical science. The increasing disadvantages and serious results to the subject due to the passage of time accompanying the development and growth of undetected malignant tumors, and the all too frequent difficulty in finding that a malignant tumor is present, have been long felt serious problems.

Certain smear tests and biopsies provide some help in diagnosis for certain malignant tumors, but all too often only when the tumors have progressed to an undesirable stage, requiring serious surgery with undesirable prognosis. The problems for the most part still remain unsolved. Thus, the long-felt and serious need remains, and the long search continues, for an effective diagnostic means to enable not only improved, but particularly also early, detection of the presence of a malignant tumor condition.

SUMMARY OF THE INVENTION

In accordance with the present invention, malignant cancer in most of its stages, but especially in its initial stage, can be detected, regardless of its location in the body.

The invention involves (a) a glycoprotein-polysaccharide-like antigenic substance derived from cancer cells; (b) cancer detection preparations comprising a mixture of certain of these substances with the blood serum of the patient to be tested; and (c) a testing procedure wherein the preparations are intradermally injected into the patient and the resultant erythema (redness) measured.

The glycoprotein-polysaccharide-like antigenic substances are derived from a mitochondrial fraction of selected cancer cells. These substances are preferably prepared from carcinoma, sarcoma, and lymphoma cells and treated to enhance cancer specificity and sensitivity.

The cancer detection preparation is made by mixing at least one of the above antigenic substances with blood serum from the patient. Preferably, each of the antigenic substances (carcinoma, sarcoma, lymphoma) is combined with blood serum which has been specially treated to remove antibodies produced in response to the presence of non-cancerous antigens. Two such sets of preparations are preferably made with one set using serum treated with a proteolytic enzyme (e.g. trypsin), and the other set using untreated serum.

The testing procedure involves injecting intradermally (a) one or more of the above preparations, and (b) the patient's serum which serves as a control. Where a proteolyticized preparation is used, a proteolyticized serum control is also used. Preferably, both proteolyticized and non-proteolyticized serum complexes of all three antigenic substances are injected. The patient's reaction to the injections, manifested by erythema, is measured physically as an indicator of the presence or absence of cancer.

DETAILED DESCRIPTION

The term "cancer" is used herein in its broad sense to embrace any malignant tumor. The early stage of a cancer is referred to as its incipient stage and/or as an incipient cancer.

In the above-mentioned parent applications, the glycoprotein-polysaccharide-like antigenic substances of the invention are referred to sometimes as GPAS or IGPAS (when a certain chromatographically separated fraction is used). Hereinafter, for the sake of consistency with current terminology, each of the antigenic substances manufactured in accordance with the preferred embodiment of the invention is referred to as TPS (for tumor polysaccharide substance). TPS 1 is the antigenic substance derived from carcinoma; TPS 2 is derived from sarcoma; and TPS 3 from lymphoma.

A. Preparation of Initial Antigenic Substance

The preparation of TPS involves first the derivation of an initial glycoprotein-polysaccharide-like antigenic substance from cancer cells. Essentially, this initial antigenic substance comprises the mitochondrial fraction of the cells from which lipids and proteins have been removed as described below. The antigenic substance can be manufactured from animal or human cancerous tissues although human tissue is preferred since it has fewer viruses. Generally speaking, primary cancers or cancer recurrences at the primary site are preferred although it is believed that metastatic cancers could be used as well. Moreover, all forms of cancer can be used, but, in accordance with the preferred embodiment, the antigenic substances are derived from carcinoma (TPS 1), sarcoma (TPS 2) and lymphoma (TPS 3).

In deriving TPS 1, carcinoma of the lung is preferred since it has relatively little fat and other extraneous tissues. It currently appears that any form of sarcoma or lymphoma can be used. The process as described in the following is the same for each of TPS 1, TPS 2 and TPS 3.

1. Separation of Mitochondrial Fraction

After the selected cancerous tissue is obtained (for example by resection) from a human harboring the cancer, it is examined microscopically to verify the type of cancer. It is then disintegrated to rupture the cell membranes so that the mitochondrial fraction of the cells can be separated from the cell membranes and nuclei. Removal of the cell membranes and nuclei is an important step since they contain DNA which should be removed for purposes of safety.

The cancer cells may be disintegrated as indicated above by grinding, and advantageously homogenizing, the selected tissue in 0.1 molar saline (i.e. sodium chloride) solution or distilled water to provide a suitably centrifugable material, preferably an homogenate (referred to hereinafter for purposes of discussion) of from 15 to 50% solids by weight, optimally of about 20% (e.g., 4 ml saline to 1 g tissue). The homogenate is centrifuged in a refrigerated centrifuge at a temperature of about 0°–5° C. at a sufficient speed to throw down the cell membranes and nuclei. For example, the homogenate may be centrifuged at a speed of about 1000 to about 3500 r.p.m. (equivalent to 110 to 1200 g) for from about 2 minutes to about 30 minutes and beneficially from about 15 to 20 minutes. The sediment is discarded.

The supernatant liquid is then centrifuged at from about 9000 to about 15,000 (equivalent to 8500 to 26,000 g), and optimally at about 10,000, r.p.m. (equivalent to 10,000 g), for from about 10 to 30 minutes to cause the sedimentation of the mitochondrial fraction.

These sedimentations can be carried out at any temperature below that at which enzymatic action occurs, i.e., between about zero and 25° C. and optimally from zero to about 5° C.

2. Glycoprotein-Polysaccharide Isolation

The mitochondrial fraction contains lipids and proteins which tend to reduce the specificity of the TPS as a cancer-detecting agent. Accordingly, it is desirable to isolate the glycoproteins and polysaccharides from the dispersion. This can be done by known processes of the type used to extract pneumococcal polysaccharides from bacteria. Two such processes are described in the following sections 2.(a) and (b).

a. Preferred Method

The mitochondrial sediment is dispersed in a physiological saline solution to its original volume. The mitochondrial dispersion is then mixed with from about 0.1 to about 5 times its volume (optimally about 0.5 volume) of an organic lipid solvent, e.g. diethyl ether. The mixture is vigorously agitated for a sufficient time to dissolve the lipids, for example, from about 5 to about 10 minutes. The mixture then is allowed to stand to separate into its ether and aqueous phases. The ether layer (containing the lipids) is discarded. The procedure can be repeated several time to ensure removal of the lipids.

Aqueous alkali is added to the drawn off aqueous phase to raise its pH to above 7 and the temperature is raised to from about 80° C. to boiling for a time sufficient to hydrolyze the proteins. For example, sodium hydroxide solution may be admixed to the aqueous phase in an amount sufficient to provide alkali corresponding to from about 10% to about 15% by volume, calculated as 2N NaOH, and the mixture heated in a water bath at 100° C. for about 30 minutes.

The mixture containing the hydrolyzed protein is then cooled and dialyzed through a membrane which will pass the low molecular weight compounds and retain the high molecular weight compounds of the hydrolysate. Such a membrane may have a pore size which excludes compounds having a molecular weight of 3500 or more. The time of dialysis may be about 2 hours at a conveniently safe temperature, for example, from zero to about 25° C. and optimally at from about freezing to about 5° C. The mixture may be dialyzed against distilled water or advantageously a buffered phosphate saline solution (e.g. at pH 6.8 and composed of 0.81 g., i.e. gram, Na$_2$HPO$_4$, 1.04 g. KH$_2$PO$_4$, 6.8 g. NaCl, in 1 liter distilled water.)

The high molecular weight dialysis residue contains the initial glycoprotein polysaccharide-like antigenic substance. The residue is shaken or stirred together vigorously in from about 0.25 to about 5 volumes, and optimally about equal volumes, of a protein-denaturing agent (for example, chloroform containing 2% n-octanol) in which the protein and the glycoprotein-polysaccharide-like antigenic substances are insoluble, for a sufficient time (from about 1 to 15 minutes, optimally about 10 minutes) to denature the protein. The mixture is then separated into chloroform and aqueous layers, advantageously by centrifugation at a speed sufficient to expedite phase separation, for example, about 1000 r.p.m. (or less) to about 3000 r.p.m., for about 10 to 30 minutes. The denatured protein collects at the interface of the two layers and the protein and heavier chloroform layer are discarded. The chloroform extraction is repeated as often as necessary until two consecutive separations show no protein at the interface.

The clear aqueous phase contains the desired initial glycoprotein-polysaccharide-like antigenic substance. The Molisch test for sugar and the Dische test for nucleic acids may be conducted as described in Kabat and Mayer "Experimental Immunochemistry", 2nd edition, pages 526–527 and 553 respectively. These tests are not necessary but, if conducted, should be positive for the Molisch test and negative for the Dische test.

b. Alternate Method

An effective alternate method for isolating the initial glycoprotein-polysaccharide-like antigenic substance involves suspending the mitochondrial sediment from the high speed centrifuge in a buffer solution such as acetate buffer (e.g. 157.5 gm. of NaC$_2$H$_3$O$_2$·3H$_2$O in 3 liters of distilled water) and adjusting the pH to about 6 with a compatible acid, e.g. glacial acetic acid. This suspension is frozen and ground, preferably slowly to avoid undue temperature rise, and thereafter heated merely enough to melt it. The ground suspension then is centrifuged at a speed of at least about 10,000, and preferably between about 15,000 and about 20,000 rpm.

The supernatant is withdrawn and the sediment discarded. Several volumes of a water-miscible precipitant for polysaccharides and glycoprotein-like substances , e.g. about 5 volumes of cold isopropanol, are admixed with the supernatant to precipitate the polysaccharides and glyco-protein-like substances. The precipitate is separated and the supernatant discarded.

This precipitate is dissolved in cold distilled water and the resulting turbid greenish solution is deproteinized by compatible deproteinization such as the Sevag method, Biochemische Zeitschrift, volume 273 (1934) page 319 (see Example 3).

This initial antigenic substance isolated in accordance with either of the above procedures disperses readily in water or aqueous saline solutions to give a stable, non-dialyzable solution at a molecular weight cutoff of 3500; is stable in 0.18 molar saline solutions at from about 0° to 5° C.; is precipitated from aqueous medium by isopropanol and insoluble in isopropanol; behaves like a glycoprotein (and so is called "glycoprotein-polysaccharide-like") giving a positive Molisch test and negative Dische test; on hydrolysis with dilute sulfuric acid at about 100° C., followed by de-ionization as with a cationic ion exchange resin such as 'Dowex-50', yields a hydrolysate containing identifiable sugars; and on finite analysis shows amounts of amino acids typical of glycoproteins.

B. Enhancing Cancer Specificity and Sensitivity (Preparation of TPS)

The initial antigenic substance can be used as the antigenic substance in the cancer detection procedure described below in Section D. However, when using this initial antigenic substance without further treatment, false positive indications may be found for conditions other than cancer. Such conditions include benign tumors, diverticulitis, cirrhosis of the liver, peptic ulcer, and colitis, among others. Thus, in accordance with the preferred embodiment of the invention, in order to reduce the likelihood of false positive reactions, gel chromotography is used as explained below to isolate by molecular size the fractions of the antigenic substances having the highest specificity index, i.e., those fractions which are most specific for cancer and least reactive with other diseases.

If the initial antigenic substance contains any undesirable dialyzable substances (e.g. such as peptides), the solution should be dialyzed through a membrane having a molecular weight cutoff point of 3500, such as a cellulose acetate membrane, against water under suitable conditions for a time sufficient to dialyze out substantially completely the dialyzable substances, e.g. for about 1 to 2 days at from 5° to 22° C.

Then the product of this dialyzation or of the deproteinization treatment, if it did not need dialysis, can be further processed for storage such as by drying under conditions to preserve the integrity (i.e. the effectiveness for extended use) of the product, for example, by lyophilization. The initial antigenic substance may also be stored in liquid form at a temperature of 5° C. The product, if stored in lyophilized form, when ready for further processing, can be reconstituted in an aqueous buffered solution (with a buffer such as ammonium bicarbonate, ammonium formate, or pyridine acetate of pH range from 3 to 9 and optimally between 5 and 6). A volatilizable buffer (e.g. pyridine acetate) is preferred since it will disappear if the TPS is dried (e.g. by lyophilization) for purposes of storage.

The resulting buffer solution of the lyophilized material then is fed onto a properly prepared bed of chromatographic-type gel beads effective to enable chromatographically the retention of substances within a molecular weight range of, for example, from about 2500 to about 40,000 or more. Such beads may include 200 to 400 mesh (37 to 75 microns size) polyacrylamide (copolymer of acrylamide and N,N-methylene-bisacrylamide) beads such as Bio-Gel P-30 of Bio-Rad Laboratories, of Los Angeles, Calif., dextran gel beads (40 to 100 microns) such as Sephadex G-75 of Pharmacia Fine Chemicals, Inc. of 800 Cenntennial Avenue, Piscataway, N.J., or other equivalent materials.

After the buffered reconstituted solution has passed through the gel bed, the part of it retained in the bed is eluted with an eluate buffer solution of the same constitution as that used to dissolve the lyophilization product. The elution profile of the resulting column eluate solution is determined from a series of suitable small volume fractions collected as in a fraction collector, for example, (a) by the Lowrey Protein Method (O. H. Lowrey, Jr. Biolog. Chem. 1951, vol. 193, p. 265) or the Bio-Rad Protein Assay (Bio-Rad Laboratories, above) or (b) by monitoring the column effluent by an ultraviolet detector. Then the fractions exhibiting the highest effectiveness (i.e. cancer specificity), specifically those fractions found to correspond approximately to the middle third of the main broad peak of the elution profile, are pooled. These pooled fractions are what is referred to herein as TPS. The same procedure is used to make TPS 1, TPS 2 and TPS 3.

Each TPS (i.e. TPS 1, TPS 2 and TPS 3), in addition to exhibiting the properties of the initial glycoprotein polysaccharide-like antigenic substance, is optically active; forms white to amber powder when lyophilized; shows molecular weights from about 3500 to about 50,000 as determined by gel chromatography; remains stable for at least ten years when held at 5° C. in liquid form; is stable to autoclaving; and yields patterns typical of sugars and amino acids on analysis by nuclear magnetic resonance and by gas liquid chromatography.

In comparison to the initial antigenic substance, each TPS shows much less heterogeneity under iso-electric focusing, and one-half the optical density in ultraviolet absorbance (at 280 nm.). Under NMR examination, different molecular configurations of the sugars and amino acid moieties and a lesser amount of amino acid moieties were observed.

C. Preparation of Serum

The cancer detection preparation according to the invention is a combination of the initial antigenic substance, preferably the TPS, and the patient's blood serum. The serum may contain normal, inflammatory and benign antibodies which can evoke positive reactions to the test procedures of the invention. Such antibodies include those directed against liver cirrhosis, peptic ulcer, diverticulitis, ulcerative colitis and solid benign tumors, among others. Ideally, the serum should be treated to remove these non-cancer producing antibodies which might tend to give a false positive test result.

1. Removal of Non-Cancerous Producing Antibodies

To remove the undesired antibodies, a pool of corresponding antigenic non-cancer producing substances is derived from human tissue. These antigenic substances include normal, inflammatory and benign antigens (referred to herein as NIB antigenic substances) as described in further detail below. Each of these NIB antigenic substances is derived in the same fashion as TPS, starting with tissues containing the particular antigen involved.

In a preferred embodiment, two pools of NIB antigenic substances are prepared. The first pool contains equal amounts of antigenic substances derived as described above from diverticulitis, liver cirrhosis, uterine fibroid and normal lung tissue. This shall be referred to as pool "A". The second pool contains equal amounts of antigenic substances, derived as described above, from colonic polyps, fibrocystic breast disease, ulcerative colitis, stomach ulcer and hypertrophy of the prostate and is referred to as pool B.

The antigenic substances of pool A, in a dilute aqueous gluteraldehyde solution, are used to coat the walls of a suitable plastic tube. Similarly, two groups of compatible plastic beads (e.g. polystyrene beads of diameter between 0.4 and 0.7 mm) are likewise coated, one with a like solution of group A and the other with a like solution of group B. These beads are then pooled and placed in the coated tube. The serum to be used to make the cancer detection preparations is then contacted with the antigens coating the walls of the plastic tube and the beads to remove from the serum the antibodies corresponding to the selected NIB antigenic substances of pools A and B. Alternatively, the coated plastic beads may be placed in uncoated glass tubes to avoid absorption of serum antibodies by the plastic tubes.

2. Proteolyticizing the Patient's Serum

In the preferred embodiment of the invention, each of TPS 1, TPS 2, and TPS 3 is separately mixed with the patient's blood serum both proteolyticized and non-proteolyticized. It is theorized that a proteolytic enzyme (such as trypsin) when present in sufficient quantities in the patient's blood serum, frees antigen reactive sites on the cancerous antibodies and/or splits antigen-antibody complexes so as to provide free antibodies for interaction with the TPS. The quantity of the enzyme must not be so high as to result in a proteolytic enzyme content that will degrade the desired antibodies in the serum.

In the preferred embodiment, trypsinized serum is prepared by admixing some of the patient's diluted blood serum, either before or after removal of NIB antibodies as described above, with the desired concentration of pharmaceutically parenterally acceptable trypsin. Preferably, the serum is diluted in an isotonic saline solution.

D. The Testing Procedure

In the preferred embodiment, and as described in detail below, each of TPS 1, TPS 2, and TPS 3 is mixed with the patient's trypsinized serum and with the un-trypsinized serum, yielding a total of six cancer detection preparations. These six preparations are separately injected intradermally into the patient. In addition, the patient receives control injections of both trypsinized and untrypsinized serum, making a total of eight injections. The procedure for making the test preparations is now described. The same procedure is used for each of TPS 1, TPS 2 and TPS 3.

As a preliminary step, the TPS must be made safe for injection. This may be done, for example, by passing the TPS through a Seitz filter to remove any bacteria and then subjecting the Seitz filter filtrate to terminal sterilization by autoclaving for about 20 to 50 minutes (optimally 30 minutes) at 121° C. and 1 kg/cm² pressure, as a safeguard against any viral contaminants. This sterile filtrate is adjusted to a suitable dilution in physiological saline solution as described below.

The trypsinized serum is admixed with equivalent volumes of each of TPS 1, TPS 2 and TPS 3 dispersed in compatible dilutions in isotonic saline solution. As mentioned above, it is theorized that the trypsinized serum complexes with the TPS at the reactive sites of the serum antibodies. Thus, the mixtures are allowed to stand long enough to permit this complexing reaction to take place. The complexing reaction is quite rapid so that often only a few minutes is sufficient; however, no apparent harm occurs if the complexed product resulting from the admixed trypsinized serum and TPS stands up to 48 hours at 4° C. By way of example, the mixture may stand from one to 60 minutes at a temperature from 0° to about 38° C. Optimally, the mixture may stand for 30 minutes at a temperature of 5° C.

The patient's non-trypsinized serum is also mixed with each of TPS 1, TPS 2 and TPS 3. Prior to mixing, the non-trypsinized serum should be diluted with a sterile isotonic sodium chloride aqueous solution to the same dilution as the tryspinized serum. The diluted trypsinized and non-trypsinized serum may be used, as described below, as the control injections.

E. The Injections

To recapitulate, in the preferred embodiment, eight separate preparations are injected intradermally into the patient to be tested. These eight preparations include, respectively, TPS 1, TPS 2 and TPS 3 admixed with the patient's diluted trypsinized serum, and TPS 1, TPS 2 and TPS 3 admixed with the patient's diluted non-trypsinized serum. In addition, there are two controls comprising the patient's diluted trypsinized serum and the patient's diluted non-trypsinized serum. Each preparation (including the controls) may be injected, for example, in an amount between 0.05 ml and 0.2 ml, preferably 0.1 ml. The intradermal injections can be on any open skin area of the body but are preferably on both sides of the back between the small of the back and the neck. The controls, composed of comparable concentrations of the prepared serum and the prepared proteolyticized serum of the subject are injected at similar sites on the back.

An erythema reaction develops rapidly at the site of each injection. The comparative areas (from test and control injections) can be measured within 1 to about 5 minutes after injection, preferably at 1.5 minutes.

In each case, the immediate reactions at the injection sites, manifested by erythema (even minimum erythema), are measured (preferably about 1.5 minutes after injection) in millimeters along the longest diameter and so also along the longest diameter normal to this first one. This is done for each injection site. For each TPS erythema there then is calculated the ratio of (A) the mean (average) of the larger and the smaller diameters to (B) the mean determined from like diameter measurements of the corresponding control erythema. A ratio of 1.35 or above for any one TPS injection is a positive indication of cancer presence in the patient. A ratio below 1.35 indicates a negative result.

F. Establishing Activity Levels

There are limits to the amount of TPS which should be injected to obtain meaningful information based on a comparison of the mean diameters of the test and control erythemas. If the level of TPS is too low, a response may not be obtainable. If the level is too high, the presence of excess TPS (an antigenic substance) may inhibit the formation of an erythema. Except for these general requirements, the potency of the injected TPS is not critical and the relationship of potency to the size of the erythema is not known. Certain techniques have been developed to "standardize" or establish an activity level of the TPS produced in accordance with the foregoing procedures so that the skin test can be performed in the manner described. An in vitro anaphylactic test is useful in ensuring that the activity level of the injected TPS falls within the proper limits. Since the test and the standardization procedure in themselves form no part of the basic inventions, they are only described generally in the following sections of this specification.

1. The Test

A modified Schultz-Dale test can be used to establish an activity level for each TPS such that it can be used in the skin tests.

The Schultz-Dale technique is a known process for detecting the immunogenicity of substances. The conventional test is modified in order to detect the presence of polysachharide and glycoprotein-like antigens in low concentrations. This is done by the use of adenosine triphosphate (ATP) to enhance the sensitivity of the test so that amounts of antigen as small as $10^{-11}$ to $10^{-14}$ micrograms ($\mu$g) can be measured. The test, in broad outline, is as follows.

A virgin female guinea pig is immunized with TPS. The animal is sacrificed one to three days later and a uterine segment obtained.

The uterine segment is bathed in 10 ml of an aerated Tyrode's solution with a calcium concentration of 0.1 g/l. The muscle is connected to a strip chart recorder to record its contractions. ATP is added in increasing doses starting at 5 $\mu$gs until a response (muscle contraction) is obtained. The bath is then drained and replaced with Tyrode's solution containing 75% of the amount of ATP that caused the response. This level is considered the baseline.

If no muscle reaction is obtained with 1000 $\mu$g of ATP, the calcium level is increased and the procedure repeated until a baseline is determined. By appropriate adjustment of the level of ATP and/or calcium, the sensitivity of the uterine segment can be greatly enhanced. After the baseline is determined, the antigenic substances are added to the bath (e.g. in 0.25 ml amounts) at known dilutions (as explained below).

2. Setting the Activity Level

If one has the initial antigenic substance of a known activity level, i.e. a "standard", a TPS of unknown activity level may be compared with the standard and the unknown diluted so that its activity level (as measured by the modified Schultz-Dale test) approximates the activity level of the standard. Where such a standard is not available, it is possible to adjust the activity level by comparing the purified TPS (after gel chromatography) with the crude or initial antigenic substance, for example, as recovered after separation of the chloroform and aqueous layers following chloroform deproteinization as described in Example 6.

The initial antigenic substance produced as described herein can be used successfully for the skin test if diluted 400 to 1. If the initial antigenic substance is produced in accordance with the examples given in this specification, the substance itself will be diluted by about 3–4 to 1 (depending on the amount of water lost during the chloroform separation step). This means that the substance as injected (assuming 400 to 1 dilution) will be diluted by a factor between 4800 and 6400. Practically speaking, starting with one gram of cancerous tissue, about 0.25 mg of initial antigenic substance will be dissolved in between 1200 and 1600 ml saline solution.

After the modified Schultz-Dale test has been set up and the baseline determined as described above, the activity level of the "standard" is determined. Starting with a dilution, for example in the order of $512 \times 10^9$, the standard is tested to determine whether a response (i.e. a muscle contraction) can be obtained. The dilution may then be decreased successively by a factor of two (i.e. successive dilutions of $256 \times 10^9$, $128 \times 10^9$, etc.) until a response finally is obtained. Typically, a response will be obtained at a dilution of $64 \times 10^9$ or above, possibly as high as 2 to $4 \times 10^{12}$.

Once the response of the standard is known, the unknown TPS (e.g. as produced in accordance with Example 6 below) is tested in the same way using the same test procedure and muscle segment(s). Typically, the titer (maximum dilution given a response) of the unknown TPS will be 10,000 to 15,000 times the titer of the standard for which a response was obtained. Whatever that titer is, that is the extent to which the purified TPS must be diluted to approximate (for purposes of a skin test) the desired activity level. In Example 7 below, reference to TPS "diluted to the desired activity level" refers to TPS which has been diluted as described herein to correlate approximately with a desired "standard" (e.g. the initial antigenic substance diluted 1 to 400).

The several portions of the invention are illustrated by, but not restricted to, the following examples wherein, as in any of the claims, all temperatures are in centigrade unless otherwise noted, and liquid products which are to be included in preparations to be injected are to be processed at a suitable stage under conditions whereby the preparation to be injected is in an sterile state.

EXAMPLE 1

Separation of Mitochondrial Fraction from Cancer Cells

Cancer tissues, i.e. carcinoma, fibrosarcoma and lymphoma, obtained by resection from a human harboring such cancer were separately disintegrated by homogenizing in 0.2N saline (NaCl) solution to provide homogenates of about 20% solids. Each homogenate was centrifuged in a Model B-20 (International Equipment Company) refrigerated centrifuge at a temperature of about 4° C. at about 3,000 r.p.m. for 15–20 minutes. The sediment was discarded.

The supernatant liquid was centrifuged at about 10,000 r.p.m. for about 10–30 minutes at 0°–5° C. to cause the sedimentation of the mitochondrial fraction. The sediment, containing the mitochondrial fraction of the cancer cells, was separately dispersed in 1-normal saline.

EXAMPLE 2

Isolation of Glycoprotein-Polysaccharide-Like Substance

The three saline dispersions from Example 1 were respectively mixed with equal volumes of diethyl ether and vigorously agitated for 5 to 10 minutes to dissolve lipids. After standing, the ether phase containing the lipids was separated from the aqueous phase and discarded.

A 2N aqueous sodium hydroxide solution in an amount of from about 10% to 15% by volume, was added to the drawn off aqueous phase to increase the pH to above 7 and the temperature was elevated to a temperature of about 100° C. in a water bath for 30 minutes. The hydrolysis mixtures were cooled and dialyzed through a membrane having a 3500 molecular weight cutoff for about 2 hours at a temperature of 0°–5° C. against a buffered phosphate saline solution (at pH 6.8, 0.81 g. $Na_2HPO_4$, 1.04 g. $KH_2PO_4$ and 6.8 g. NaCl in 1 liter distilled water)

The dialysis residues were shaken in about equal volumes of chloroform for about 20 minutes to permit the denatured protein to collect at the interface. The chloroform layers were separated from the aqueous layers by centrifugation at about 1000-3000 r.p.m. (or less) for about 10-30 minutes. The denatured protein at the interface and the heavier chloroform layer were discarded.

The relatively clear aqueous phase contains the initial glycoprotein-polysaccharide-like antigenic substance.

EXAMPLE 3

Isolation of Glycoprotein Polysaccharide Substance (Alternate Method)

Each 10,000 rpm sediment from Example 1, prior to dispersion in saline, was suspended in an acetate buffer of 157.5 grams of $NaC_2H_3O_2 \cdot 3H_2O$ in 3 liters of distilled water. The pH was adjusted to about 6 with glacial acetic acid. The suspension was ground, at about 0° C., slowly to avoid undue temperature rise. The ground suspension was then centrifuged at a speed of from about 15,000 to about 20,000 r.p.m.

The supernatant was withdrawn and the sediment discarded. About 5 volumes of cold isopropanol were mixed with the supernatant to precipitate the polysaccharides. The precipitate was separated in known manner, suspended in the acetate buffer and ground as above. The resulting suspension was centrifuged as before, and components of the supernatant likewise caused to precipitate with isopropyl alcohol.

This precipitate was dissolved in cold distilled water and the resulting turbid greenish solution was deproteinized by compatible deproteinization such as the Sevag method, Biochemische Zeitschrift, volume 273 (1934) page 319. Thus, 50 ml. of chloroform and 10 ml. of butyl alcohol were added to each 150 ml. of precipitate solution. This mixture was agitated in a homogenizer at about 3° C. The resulting emulsion was separated into its respective phases (aqueous and organic solvent) by centrifugation and the aqueous layer was separated from the organic layer. This Sevag procedure was repeated on the aqueous phase until the product was completely deproteinized, i.e. when no further protein precipitate was seen between the aqueous and the organic solvent layers. The initial antigenic substance then is recovered by centrifugation to break the emulsion, from which is separated the aqueous phase which contains the initial glycoprotein-polysaccharide-like antigenic substance.

EXAMPLE 4 - TPS 30 ml of the initial glycoprotein-polysaccharide-like antigenic substances of Example 2 were separately charged into a 100 ml Virtis (Virtis Company, Gardiner, N.Y., U.S.A.) lyophilization flask. Each was shell frozen in ethanol chilled to about −40° C. in a Virtis shell freezer until cracks appeared in the frozen shell.

The flask then was connected to the manifold of a (Virtis) lyophilization dryer operating at a vacuum of at least about 100 microns, with a compressor temperature of at least −20° C. (preferably −50° C.). With controlled heat applied to the drying rack, the (amorphous) ice in the frozen material was allowed to sublime completely (in about 14 hours). The vacuum then was released and the flask removed from the manifold. The lyophilized product in its container could be stored at low humidity (at 5° to 22° C.).

The lyophilized product (e.g. TPS) then was dissolved in 0.05M pyridine acetate buffer (pH 5.3) in a concentration of 3 mgs. per milliliter of buffer and fed onto a gel filtration bed (80 cm long by 2.5 cm diameter) containing a bed of polyacrylamide gel beads (200-400 mesh and fractionating range from about 2500 to 40,000) which previously had been prepared for gel filtration (for example, as known, with prewash by buffer solution alone and gel loading with elimination of trapped air).

After the passage of the lyophilized product solution in the buffer through the column was completed, the retained portion of the solute on the gel beads was eluted by passing through them the same pyridine acetate buffer at a flow rate of 6 ml per square cm of bed cross sectional area per hour. The sample profile was obtained by use of ultraviolet spectrophotometry. See, for example, Methods in Immunology and Immuno-Chemistry (1968), Vol. III, pp. 260-261 (Williams and Chase), Academic Press.

The slow stream of drops of eluate from the gel bed was monitored by an ultraviolet monitor (specifically the LKB UVICORD III, product of LKB Instruments, Rockville, Md. U.S.A.) at a wavelength of 206 nm. (i.e. nanometers) while 6 ml. sample fractions were collected seriatim in a fraction collector. The elution (U.V.) profile was automatically recorded by the monitor. The fractions found to correspond to about the middle third of the main broad peak of the profile exhibited the useful amount of the cancer detection specificity, and so constitute the respective tumor polysaccharide substances TPS 1, TPS 2 and TPS 3.

For TPS 1 (carcinoma), out of 100 seriatim fractions tested, the useful fractions were numbers 38 to 65. They were pooled. The lyophilized product derived from each of fibrosarcoma (TPS 2) and lymphoma (TPS 3), respectively, were separately dissolved in the same buffer and gel filtered in the same way. Their eluate (U.V.) profiles likewise were obtained by U.V. spectrophotometry, and selected fractions collected as with the carcinoma antigenic substance (TPS 1). The useful fractions for the fibrosarcoma (TPS 2) were numbers 61 to 70 out of 100 and they were pooled. For the lymphoma (TPS 3) the useful fractions were 46 to 65 out of 100 which also were separately pooled.

Each of these separate TPS pools was separately diluted with isotonic saline prepared from distilled (preferably four times to be definitely pyrogen-free) demineralized water, and each such substance then was ready for standardization, sterilization and use.

While the 206 nm. wavelength was used in the foregoing example, it may be found in some cases that more distinct and sharper results are obtained at another wavelength within the range of from about 200 nm. to about 280 mm. Which other wavelength then to use can be determined by simple trial, for example, by subjecting a sample of the eluate to the ultraviolet to see if any recording above the base line of the recorder occurs.

EXAMPLE 5

Proteolyticized Serum Complexed with TPS

Pharmaceutically parenterally acceptable trypsin is dissolved in pyrogen-free, sterile isotonic sodium chloride solution to a concentration of 10 $\mu$g (micrograms) of trypsin per 0.05 ml of solution. If needed, this trypsin solution is exposed to ultraviolet light for about 30 minutes for sterilization.

A solution of 20 micrograms of trypsin in 0.1 ml saline is added to 0.1 ml of a solution of one part of the blood serum of the subject to be tested diluted with 10 parts of sterile isotonic sodium chloride aqueous solution, and their mixture left for 30 minutes at 0°-5° C.

Each of the initial antigenic substances from Example 2 is diluted to one volume in 400 volumes of sterile isotonic sodium chloride solution. One volume of the latter is admixed with an equal volume of saline diluted untreated serum and with trypsinized serum. Their mixtures are allowed to stand for 30 minutes at 5° C. The solutions are ready for intradermal injection in suitable amount as above explained. The saline diluted trypsinized and untrypsinized serum are used for the control injection.

Examples 6 and 7 are the current preferred methods of making TPS and administering the skin test.

EXAMPLE 6

(a) Source of Tissue

Human tumor tissues were collected from surgery or early post-mortem examinations in a non-contaminated state. Three such tumor tissues are required.
1. Carcinoma of the lung (primary) for TPS-1
2. Sarcoma (primary) for TPS-2
3. Lymphoma for TPS-3

Each collected tissue received a histological diagnosis by a qualified pathologist.

(b) Collection of Tissue

Each collected tissue was placed in a sterile polyethylene bag. The tumor tissue identification card was completed by the responsible doctor (pathologist) at source and attached to each collection bag. The tissue was then quick frozen and kept in a deep freeze at the collection source until forwarded to the tissue bank. The tissues were transported in a refrigerated container to a frozen tissue bank.

(c) Extraction

The tissue was extracted aseptically as follows:

(i) Tissue homogenization

Using sterilized tissue forceps, scissors, stainless steel trays and while wearing surgical smocks, the thawed tumor tissue sample was carefully separated from any adjacent normal tissue. The separated tumor tissue was then divided into small pieces (approximately 5 mm×5 mm) to facilitate homogenization and to allow careful examination of the tumor mass for homogeneity and the absence of deep necrotic abscesses or other deleterious degenerative processes.

The tumor tissue segments were weighed and washed several times with sterile hypotonic saline solution. The volume equivalent of the weight of the segments is referred to herein as the "original volume", e.g. 10 grams tissue corresponds to an original volume of 10 ml. The washed tumor tissue segments were combined with 4 original volumes of cold hypotonic saline solution (0.1 M) and homogenized for 30 minutes in a Virtis homogenizer (immersed in crushed ice) at 35,000-40,000 rpm.

(ii) Centrifugation

The homogenate was centrifuged twice at 3,000 rpm at 5° C. for 10 minute periods. The sediments were discarded. The supernatant was then centrifuged at 10,000 rpm at 5° C. for 20 minutes. The supernatant was discarded and the sediment resuspended to four times original volume with normal saline solution (0.9% NaCl - pyrogen-free).

(iii) Total Lipid Extraction

The resuspended sediment was combined with an equal volume of ether and vigorously shaken in a separatory funnel for 5 minutes. The aqueous phase was separated from the ether phase.

(iv) Alkaline Deproteinization

Nine volumes of the aqueous phase was combined with one volume of 2N NaOH. The mixture was kept in a water-bath at 100° C. for 30 minutes.

(v) Dialysis

The solution obtained from stage (iv) was allowed to cool and then transferred to a bag of cellophane dialysis tubing. The bag was stirred in a large volume of phosphate-buffered saline at 4° C. For about 40 ml of original aqueous phase, the buffer was changed four times at 30 minute intervals.

(vi) Chloroform Deproteinization

The dialyzed solution from the bag was combined with an equal volume (e.e. about 40 ml) of chloroform containing 2% n-octanol and vigorously shaken in a separatory funnel for five minutes. The aqueous phase was centrifuged at 2,000 rpm for 10 minutes and the aqueous layer carefully drawn off from the residual chloroform layer. The chloroform layer was discarded. This procedure was repeated 8-12 times until no further precipitate was observed at the interface. This aqueous phase contained the initial antigenic substance.

(vii) Bio Gel Fractionation

Using a column packed with polyacrylamide gel beads (Bio-Gel P-30, Bio-Rad Laboratories, Richmond, Calif. 94804), each initial antigenic substance was fractionated on the basis of molecular size into multiple uniform fractions using the procedure described in Example 4 except ultaviolet profiles of the fractions were not obtained. The fractions, selected on the basis of activity level as measured by the above-described modified Schultz-Dale test, were 38 to 65 (TPS 1), 61 to 70 (TPS 2) and 46-65 (TPS 3).

(viii) Filtration and Terminal Sterilization

The TPS was then filtered through a membrane filter of 0.2 micron pore size (Nalgene Filter Unit) and standardized for potency and identity. Tween 80, presterilized by autoclaving, was added at 50 ppm. Under sterile precautions, the TPS was distributed into 1 ml ampules. After sealing, the ampules containing TPS were given terminal sterilization at 1 kg/cm$^2$ pressure and 121° C. for 20 minutes.

(x) Storage

The TPS material was then stored at 5° C. When shipped, TPS ampules are shipped cold.

EXAMPLE 7 (The Test)

(a) Serum

Blood was obtained from a vein of the patient to be tested, allowed to clot and the serum separated. Immediately before use one part of the serum was diluted in 12 parts sterile 0.9% NaCl solution.

(b) Removal of NIB Antibodies

Each of the NIB pools A and B prepared as described above in section C.1. was diluted in a solution of sterile isotonic sodium chloride solution to a desired activity level. Each dilute NIB pool was mixed with 25% aqueous gluteraldehyde in a ratio of 4 to 1. This working solution is referred to below as the NIB-g pool.

0.2 ml. of NIB-g pool A was added to sterile styrene acrylonitrile tubes of 12×75 mm. The solution was maintained for 24 to 48 hours at room temperature with gentle constant agitation. The NIB-g solution was decanted and the tubes rinsed with sterile isotonic sodium chloride solution. The rinse was discarded, the tubes dried under ultraviolet light, and the tubes capped with sterile caps. These coated tubes were stored and transported at 5° C.

The beads used in this process were polystyrene DVB beads with a diameter between 0.4 and 0.7 mm. They were carefully washed and autoclaved. Half were then coated with the NIB-g pool A and the other half with the NIB-g pool B. This may be done in a sterile closed flask at ambient temperature with gentle constant agitation for 24 hours. The pools were decanted, and the coated beads rinsed with sterile saline. The two sets of coated beads in saline rinse were then combined, decanted and swirled in a sterile saline rinse at 150-200 RPM at room temperature for 15 minutes. The rinse was then removed and the beads dried.

The dry beads were then dispensed in 0.2 mg amounts into the coated polystyrene tubes. The serum of the patient to be tested was then diluted in 0.15M sterile saline solution. For example, 0.1 ml serum may be diluted with 0.9-1.2 ml saline solution. The diluted serum was added to the plastic tube containing the beads and subjected to mild shaking for 60 minutes at 37° C. The serum was then removed so that it could be used in the skin test.

(c) Trypsin Solution

Lyophilized trypsin was dissolved in sterile isotonic saline solution to give a final concentration of 0.2 mg/ml.

The patient's diluted blood serum (from b) was mixed with an equal volume of the trypsin solution (from c) and the mixture left for a period of 30 minutes at 5° C. to ensure trypsinization. To each of four test tubes (A, B, C, D), 0.1 ml of this mixture was added.

The diluted serum (from a) was also mixed with an equal volume of saline (without trypsin) and the mixture left to stand for the same period of time at the same temperature, i.e. for 30 minutes at 5° C. To each of a second set of four test tubes (E, F, G, H), 0.1 ml of this non-trypsinized mixture was added.

TPS 1, TPS 2 and TPS 3 diluted to the desired activity level was then added in equal amount (e.g. 0.1 ml) to the tubes as follows:
TPS 1 to Tubes B and F
TPS 2 to Tubes C and G
TPS 3 to Tubes D and H To the control tubes A and E, 0.1 ml of saline alone was added.

The mixtures of serum and TPS were left for an incubation period to ensure complexing of the TPS antigen with the serum antibodies for at least 30 minutes at about 5° C.

(d) Performance of the Test

The skin test consists of eight injections. Of these, two are control injections: untreated serum and trypsinized serum. Of the remaining 6 injections, 3 are complexes of the separate TPS's with untreated serum, and 3 are complexes of the separate TPS's with trypsinized serum.

At the end of the final incubation period, 0.1 ml of the contents of each tube was transferred to a correspondingly numbered tuberculin syringe (one ml) fitted with a 25-gauge hypodermic needle. On the subject's back the sites for injections A-D were located and numbered with a marking pen along the line parallel with and 7.5 centimeters to the left of the spinal column. Sites for injections E-H were located and numbered with a marking pen along a line parallel with and 7.5 cms to the right of the spinal column. The first injection on either side was located on a line approximately 7.5 cms below the prominence of the seventh cervical vertebra, and subsequent injections were spaced approximately 5 cms apart. The skin area was cleaned gently with a cotton swab impregnated with acetone.

After ninety seconds from the beginning of the administration of the first injection, the tests were read in sequential order, starting with the site first injected and ending with the site last injected. In this way, the variation of time elapsing between the intradermal injection and the measurement of erythema was reduced to a minimum. A marking pen was used to indicate the limits of the longest diameter of erythema and also the diameter at right angles to it at each injection site. Measurements of the erythema diameters were then made and recorded. The longest diameter of each bleb was also measured as a check to identify gross errors in the injection procedure. The mean diameter of erythema was obtained for each of the eight injections.

The ratios of the mean diameter of erythema of the TPS-serum injection (trypsinized or non-trypsinized) to that of the appropriate serum control were then computed. A ratio of 1.35 or above for any of the TPS-serum injections constitutes a positive result.

The trypsin of Example 7(c) can be replaced by equivalent amounts of another proteolytic enzyme of animal, plant, or bacterial origin, such as chymotrypsin, papain, bromelin, streptokinase or streptodornase, and the steps of that example repeated separately respectively as to each of them to yield correspondingly effective preparations as outlined hereinbefore.

So also the cancer tissue used as starting material can be replaced by other cancer tissue and its various steps and those of the examples repeated respectively, thereby providing respectively correspondingly effective preparations.

The various cancer-detection preparations of the invention, are effective in testing for the presence of malignant tumor anywhere in the body. As initially stated, the skin test does not identify the cancer type. Similar test results can be obtained by using like preparations obtained by starting with other cancer tissue, such as melanoma tissue, for cross-reactive antigens may occur in all types of cancer tissue It has been found that by using separate antigenic substances prepared from, respectively, cancer tissues of each of the three main cancer subgroups, i.e. carcinoma, lymphoma and sarcoma, the test method of the invention is also effective in detecting other types of cancer, such as leukemia, glioblastoma, astrocytoma, multiple myeloma, polycytemia, mesothelioma and mixed tumors of the parotid among others, some to a greater degree than others.

There is no restriction as to source of the starting cancer tissue for use in producing the cancer-detection preparations of the invention. Such tissue can be taken from humans, for human testing, or other animals for animal testing and even from tissue culture sources.

While the above description of the test includes intradermally injecting the prepared blood serum of the subject to be tested into the same subject, there need be no restriction to it.

While the initial use of the cancer-detection preparations of the invention has been with humans, the tests nonetheless also can be used in veterinary medicine similarly to detect a cancer condition. The latter use need not necessarily be confined to cancer-detection preparations produced from cancer tissues derived from veterinary animals, for such preparation derived by using cancer tissue from humans are suitable for use in veterinary medicine. So also, because of the observed immunological similarity between mouse sarcoma and human sarcoma in a Shultz-Dale test, in theory, cancer-detection preparations obtained by starting with animal tissue, e.g. mouse sarcoma tissue, could conceivably be used in humans to detect a cancer condition.

Repeating tests on a subject found to be harboring a cancer, with cancer-detection preparations made from other specific cancer tissue serves to enhance the diagnosis for early detection of recurrence.

While these various detection preparations of this invention have been said to be used by intradermal injection, they also can be used by other test procedures involving antigen-antibody reactions, such as agglutination, complement fixation, and precipitation of latex or other colloidal particles. These detection preparations can be used even by the more sensitive procedures involving antigen-antibody interactions, such as radioimmunoassay, enzyme-linked-immunosorbent assay, modified invitro anaphalaxis, immunofluorescence, or any other system which could be used to detect or monitor antigen-antibody interaction.

Cancer-detection preparations which used only the initial glycoprotein polysaccharide-like antigenic substance (with or without proteolyticized serum) gave positive results with 60% of the subjects who had liver cirrhosis, peptic ulcer, diverticulosis, ulcerative colitis or solid benign tumors. Such results would necessitate conducting with those subjects additional, different tests for whichever of these other ailments is involved. However, the necessity for any such other tests is substantially reduced by using cancer detection preparations of TPS admixed with serum prepared by removing unwanted antibodies.

What is claimed is:

1. An intradermally administrable cancer-detection preparation which comprises the combination of (a) a glycoprotein-polysaccharide-like antigetic substance derived from cancerous tissue and which disperses readily, and is stable, in cold to boiling water and in aqueous saline solution, is non-dialyzable at a molecular weight cutoff point of 3500, inert to alkali and to isotonic phosphate buffered saline solution, precipitated from aqueous medium by isopropanol and insoluble in it, ether, chloroform, and butanol, gives a psoitive Molisch test and negative Dische test, and on hydrolysis with dilute sulfuric acid at about 100° C., followed by deionization, yields a hydrolysate containing identifiable surgars and on finite analysis shows trace amounts of amino acids typical of N-glycoproteins; said substance being in an aqueous vehicle, and (b) the blood serum of a subject to be tested, said preparation when injected intradermally into a subject to be tested producing an erythema about the injection site, said blood sedum containing a diagnostically effective quantity of a proteolytic enzyme.

2. The cancer-detection preparation as claimed in claim 1, wherein the proteolytic enzyme is of animal origin.

3. The cancer-detection preparation as claimed in claim 2, wherein the proteolytic enzyme is a member of the class consisting of trypsin and chymotrypsin.

4. The cancer-detection preparation as claimed in any of claims 1, 2 or 3, wherein the amount of said proteolytic enzyme in said serum is sufficient to uncover reactive sites on the antibody molecules of the antibody-carrying portion of said serum and to split antigen-antibody complexes therein yet insufficient to degrade a substantial portion of the serum antibodies and the glycoprotein-polysaccharide-like antigenic substance.

5. A cancer detection prepartion which comprises the combination of a glycoprotein-polysaccharide-like antigenic substance derived from cancerous tissue and which disperses readily, and is stable, in cold to boiling water and in aqueous solution, is non-dialyzable at a molecular weight cutoff point of 3500, inert to alkali and to isotonic phosphate saline solution, precipitated from aqueous medium by isopropanol and insoluble in it, ether, chloroform, and butanol, gives a positive Molisch test and negative Dische test, and on hydrolysis with dilute sulfuric acid at about 100 degrees C., followed by dionization, yields a hydrolysate containing identifiable sugars and on finite analysis shows trace amounts of amino acids typical of N-glycoproteins; and shows, as compared with the glycoprotein-polysaccharide-like antigenic substance of claim 1,
  (i) much less heterogeneity,
  (ii) about one-half of the optical density by ultraviolet absorbance at 280 nanometers, and
  (iii) under nuclear magnetic resonance different molecular configuration of its sugars and amino acids moieties and a lesser amount of amino acid moieties; and
  the blood serum of the patient to be tested, said blood serum including a diagnostically effective amount of a proteolytic enyzme, and which when injected intradermally into said subject produces an erythema about the injection site.

6. A cancer-detection preparation as claimed in claim 5, wherein the proteolytic enzyme is of animal origin.

7. A cancer-detection preparation as claimed in claim 6, wherein the proteolytic enzyme is a member of the class consisting of trypsin and chymotrypsin.

8. A cancer-detection preparation as claimed in any of claims 5, 6 or 7, wherein the amount of said proteolytic enzyme in said serum is sufficient to uncover reactive sites on the antibody molecules of the antibody-carrying portion of said serum and to separate antigen-antibody complexes therein yet insufficient to degrade the serum antibodies and the glycoprotein-polysaccharide-like antigenic substance.

9. A process of preparing a diagnostic product effective in providing a cancer-detection preparation comprising disintegrating cancer tissue to rupture its cell membranes to an extent to enable their separation from the cell content, separating the nuclei and cell membranes of said ruptured cells from the cell content to isolate the cell content free of nuclei and cell membranes, treating said cell content free of nuclei and cell membranes to separate therefrom the mitochondrial fraction, removing lipid and substantially completely removing protein from said mitochondrial fraction to provide a glycoprotein-polysaccharide-like antigenic substance which disperses readily and is stable in cold to boiling water and in aqueous saline solution, non-dialyzable at a molecular weight cut-off point of 3500, inert to alkali and to isotonic phosphate buffered saline solution, precipitated from aqueous medium by isopropanol and insoluble in isopropanol ether, chloroform, and butanol, gives a positive Molisch test and negative Dische test, and on hydrolysis with dilute sulfuric acid at about 100° C., followed by dionization, yields a hydrolysate containing identifiable sugars, and on finite analysis shows trace amounts of amino acids typical of N-glycoproteins, and separating said antigenic substance chromatographically into a plurality of volume fractions based on molecular size, and selecting the fractions which are most specific to cancer as the antigenic substance.

10. A process as claimed in claim 9, wherein approximately the middle third of said volume fractions are selected as the antigenic substance.

11. A process of preparing a tumor polysaccharide diagnostic product, comprising:
  (a) disintegrating cancer tissue to rupture its cell membranes to an extent to enable their separation from the cell content,
  (b) separating the nuclei and cell membranes from said ruptured cells to isolate the mitochondrial fraction of the cell content free of nuclei and cell membranes,
  (c) treating the mitochondrial fraction with a lipid solvent to remove the lipid content thereof,
  (d) treating the lipid free mitochondrial fraction with a sufficient quantity of a hydrolyzing agent to hydrolyze hydrolyzable proteins contained in said fraction and for a time sufficient to hydrolyze said proteins,
  (e) dialyzing the resulting hydrolysate through a dialysis membrane against distilled water or buffered phosphate saline solution for a time sufficient to dialyze out the components of the hydrolysate which have a molecular weight less than about 3500;
  (f) treating the retained component with a protein-precipitating agent under protein-precipitation conditions for a time sufficient and with whatever repetitions of the protein-precipitating steps may be needed to rid the water-soluble component from the mitochondrial fraction of protein;
  (g) dispersing said lipid and protein-free residue of the mitochondrial fraction in an aqueous compatible buffer solution compatible with that residue and the below mentioned gel beads,
  (h) passing that buffered dispersion of that residue through a chromatographic column of water-insoluble gel beads inert to said dispersion and of a size sufficient to remove from the dispersion organic molecules of molecular weight less than 50,000;
  (i) passing through the column of beads carrying the organic molecules an aqueous eluant of similar constitution to the initial aqueous buffer solution, in which the protein-free residue was dispersed and in an amount and for a time sufficient to elute the organic material from the beads while collecting the resulting eluate solutions in a continuous series of small volume fractions of the eluate,
  (j) evaluating each of the fractions for its activity level as to the glycoprotein-polysaccharide-like antigenic substance; and
  (k) pooling those fractions which show a suitable effective activity level of that substance as the tumor polysaccharide, improved glycoprotein-polysaccharide-like antigenic, substance.

12. The process of preparing a cancer detection preparation comprising a mixture of a glycoprotein-polysaccharide-like antigenic substance and the blood serum of a patient to be tested, the improvement comprising removing non-cancerous antibodies from said blood serum prior to mixing it with said antigenic substance.

13. A process according to claim 12, wherein said step of removing comprises coating a coatable surface with non-cancerous antigenic substances corresponding to said non-cancerous antibodies and causing said blood serum to contact said surface.

14. A process according to claim 13, wherein said non-cancerous antigenic substances are coated onto the interior surface of a tube.

15. A process according to claim 13 or 14, wherein said non-cancerous antigenic substances are coated onto a multiplicity of beads.

16. A process according to claim 13, wherein each of said non-cancerous antigens is derived from human tissue by disintegrating the tissue, extracting the mitochondial fraction of the cells, and removing lipids and proteins from said mitochondial fraction.

17. A process according to claim 12, including the step of adding a diagnostically effective amount of a proteolyticizing enzyme to said blood serum.

18. The process of preparing a cancer detection preparation comprising a mixture of a glycoprotein polysaccharide-like antigenic substance which disperses readily and is stable in cold to boiling water and in aqueous saline solution, non-dialyzable at a molecular weight cut-off point of 3500, inert to alkali and to isotonic phosphate buffered saline solution, precipitated from aqueous medium by isopropanol and insoluble in isopropanol ether, chloroform, and butanol, gives a positive Molisch test and negative Dische test, and on hydrolysis with dilute sulfuric acid at about 100° C., followed by dionization, yields a hydrolysate containing identifiable sugars, and on finite analysis shows trace amounts of amino acids typical of N-glycoproteins and the patient's blood serum, which comprises adding a proteolytic enzyme to said blood serum, said enzyme being added in an amount (a) sufficient to act on the antibody-carrying portion of said serum to uncover reactive sites on the antibody molecules yet (b) below that which will degrade the antibody content thereof and of the antigenic substance; and admixing said resulting proteolyticized serum with said antigenic substance.

19. A process according to claim 18, including the step of removing at least some non-cancerous antibodies from said blood serum prior to said admixing step.

* * * * *